United States Patent
Kato et al.

(10) Patent No.: US 6,280,588 B1
(45) Date of Patent: Aug. 28, 2001

(54) NOX-DECOMPOSING ELECTRODE AND NOX CONCENTRATION-MEASURING APPARATUS

(75) Inventors: Nobuhide Kato, Ama-gun; Kunihiko Nakagaki, Nagoya; Satoshi Nishikawa, Chita, all of (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/451,646

(22) Filed: Nov. 30, 1999

(30) Foreign Application Priority Data

Dec. 4, 1998 (JP) .................................................. 10-346111

(51) Int. Cl.[7] ..................................................... G01N 27/26
(52) U.S. Cl. ......................... 204/425; 204/292; 204/293; 204/426; 204/427; 204/429
(58) Field of Search .................................. 204/421–429, 204/292, 293

(56) References Cited

U.S. PATENT DOCUMENTS 3,843,400 * 10/1974 Radford et al. .
4,199,425 * 4/1980 Sinkevitch .
5,672,811 9/1997 Kato et al. .
5,763,763 6/1998 Kato et al. .
5,948,964 9/1999 Kato .

FOREIGN PATENT DOCUMENTS 8-271476 10/1996 (JP) .
9-113484 5/1997 (JP) .

* cited by examiner

*Primary Examiner*—T. Tung
(74) *Attorney, Agent, or Firm*—Burr & Brown (57) ABSTRACT

Disclosed is a NOx concentration-measuring apparatus for measuring a NOx concentration by using a main pumping cell including an electrode (inner pumping electrode and outer pumping electrode) having no or low decomposing/reducing ability with respect to NOx to control an oxygen concentration in a measurement gas to have a predetermined value which substantially does not affect measurement of NOx component, and using a detecting electrode having certain or high decomposing/reducing ability with respect to NOx to decompose NOx so that an amount of oxygen produced during this process is measured, wherein the detecting electrode is a cermet electrode composed of an alloy of Pt—Rh and a ceramic component, and Pt and Rh are contained in a weight ratio of Pt:Rh=20:80 to 1:99.

2 Claims, 7 Drawing Sheets

| Pt/Rh | Temperature range of weight increase | Temperature range of weight decrease |
|---|---|---|
| 0wt%/100w% | about 500 °C to about 800 °C | about 1100 °C to about 1200 °C |
| 1wt%/99w% | about 600 °C to about 900 °C | about 1000 °C to about 1150 °C |
| 5wt%/95w% | about 600 °C to about 1000 °C | about 1000 °C to about 1150 °C |
| 10wt%/90w% | about 700 °C to about 1040 °C | about 1050 °C to about 1150 °C |
| 20wt%/80w% | about 750 °C to about 900 °C | about 1100 °C to about 1200 °C |
| 25wt%/75w% | about 800 °C to about 1100 °C | about 1150 °C to about 1200 °C |

FIG. 7

NOX-DECOMPOSING ELECTRODE AND NOX CONCENTRATION-MEASURING APPARATUS

BACKGROUND OF THE INVENTION

1. Field of the Invention

The present invention relates to a NOx-decomposing electrode having certain or high decomposing/reducing ability with respect to NOx so that NOx is decomposed to produce oxygen during this process. The present invention also relates to a NOx concentration-measuring apparatus for measuring NOx contained, for example, in atmospheric air and exhaust gas discharged from vehicles or automobiles.

2. Description of the Related Art

A technique has been hitherto known as the method for measuring NOx in a measurement gas such as combustion gas, in which the NOx-reducing ability of Rh is utilized while using a sensor comprising a Pt electrode and an Rh electrode formed on an oxygen ion-conductive solid electrolyte such as zirconia to measure an electromotive force generated between the both electrodes.

However, such a sensor suffers the following problem. That is, the electromotive force is greatly changed depending on the change in concentration of oxygen contained in the combustion gas as a measurement gas. Moreover, the change in electromotive force is small with respect to the change in concentration of NOx. For this reason, the conventional sensor tends to suffer influence of noise.

Further, in order to bring out the NOx-reducing ability, it is indispensable to use a reducing gas such as CO. For this reason, the amount of produced CO is generally smaller than the amount of produced NOx under a lean fuel combustion condition in which a large amount of NOx is produced. Therefore, the conventional sensor has a drawback in that it is impossible to perform the measurement for a combustion gas produced under such a combustion condition.

In order to solve the problems as described above, for example, Japanese Laid-Open Patent Publication No. 8-271476 discloses a NOx sensor comprising pumping electrodes having different NOx-decomposing abilities arranged in a first internal space which communicates with a measurement gas-existing space and in a second internal space which communicates with the first internal space, and a method for measuring the NOx concentration in which the $O_2$ concentration is adjusted by using a first pumping cell arranged in the first internal space, and NO is decomposed by using a decomposing pumping cell arranged in the second internal space so that the NOx concentration is measured on the basis of a pumping current flowing through the decomposing pump.

Further, Japanese Laid-Open Patent Publication No. 9-113484 discloses a sensor element comprising an auxiliary pumping electrode arranged in a second internal space so that the oxygen concentration in the second internal space is controlled to be constant even when the oxygen concentration is suddenly changed.

A cermet electrode composed of $Rh/ZrO_2$ is used for the NOx-decomposing electrode of the NOx sensor as described above. When the cermet electrode composed of $Rh/ZrO_2$ is used for the NOx-decomposing electrode, a phenomenon has been observed, in which the sensitivity is lowered in accordance with the increase in operation time.

Rh tends to be oxidized in a range of 500 to 1000° C., and it repeats the oxidation reaction and the reduction reaction depending on the oxygen concentration in the atmosphere. The NOx-decomposing electrode is peeled off from the solid electrolyte substrate due to the change in volume of Rh caused by the repetition of the oxidation reaction and the reduction reaction. As a result, the impedance of the pumping cell is increased during the use of the gas sensor, and the increase in impedance consequently causes the decrease in sensitivity to NOx.

SUMMARY OF THE INVENTION

The present invention has been made taking the foregoing problems into consideration, an object of which is to provide a NOx-decomposing electrode which makes it possible to effectively suppress the oxidation reaction and the reduction reaction of Rh, and which makes it possible to suppress the adsorption of NOx at a low temperature and the formation of alloy together with any other metal element (for example, Au).

Another object of the present invention is to provide a NOx concentration-measuring apparatus which makes it possible to effectively suppress the oxidation reaction and the reduction reaction of Rh contained in a NOx-decomposing electrode, which makes it possible to suppress the adsorption of NOx at a low temperature and the formation of alloy together with any other metal element (for example, Au), and which makes it possible to stabilize the impedance and stabilize the measurement sensitivity.

According to the present invention, there is provided a NOx-decomposing electrode having certain or high decomposing/reducing ability with respect to NOx so that NOx is decomposed to produce oxygen during this process, wherein the electrode is a cermet electrode composed of an alloy of Pt—Rh and a ceramic component, and Pt and Rh are contained in a weight ratio of Pt:Rh=20:80 to 1:99.

The cermet electrode, which is composed of the alloy of Pt—Rh and the ceramic component, is used as the NOx-decomposing electrode. By doing so, it is possible to effectively suppress the oxidation reaction and the reduction reaction of Rh contained in the NOx-decomposing electrode.

Especially, in the present invention, the ratio between Pt and Rh is Pt:Rh=20:80 to 1:99 in the weight ratio. Therefore, it is possible to suppress the adsorption of NOx at a low temperature and the formation of alloy together with any other metal element (for example, Au).

It is preferable that the ratio between Pt and Rh contained in the NOx-decomposing electrode is Pt:Rh=10:90 to 1:99 in weight ratio.

According to another aspect of the present invention, there is provided a NOx concentration-measuring apparatus comprising an oxygen pump including an electrode having no or low decomposing/reducing ability with respect to NOx, the oxygen pump being used to control an oxygen concentration in a measurement gas to have a predetermined value at which NO is not substantially decomposable, and a NOx-decomposing electrode having certain or high decomposing/reducing ability with respect to NOx, the NOx-decomposing electrode being used to measure a NOx concentration by decomposing NOx and measuring an amount of oxygen produced during this process, wherein the NOx-decomposing electrode is a cermet electrode composed of an alloy of Pt—Rh and a ceramic component, and Pt and Rh are contained in a weight ratio of Pt:Rh=20:80 to 1:99.

According to the present invention, it is possible to effectively suppress the oxidation reaction and the reduction reaction of Rh contained in the NOx-decomposing electrode. Further, it is possible to suppress the adsorption of NOx at a low temperature and the formation of alloy together with any other metal element (for example, Au). In the present invention, it is especially preferable that the ratio between Pt and Rh is Pt:Rh=10:90 to 1:99 in weight ratio.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

An illustrative embodiment of the NOx concentration-measuring apparatus including the NOx-decomposing electrode according to the present invention (hereinafter simply referred to as "NOx concentration-measuring apparatus according to the embodiment") will be explained below with reference to FIGS. 1 to 7.

Figure 1:
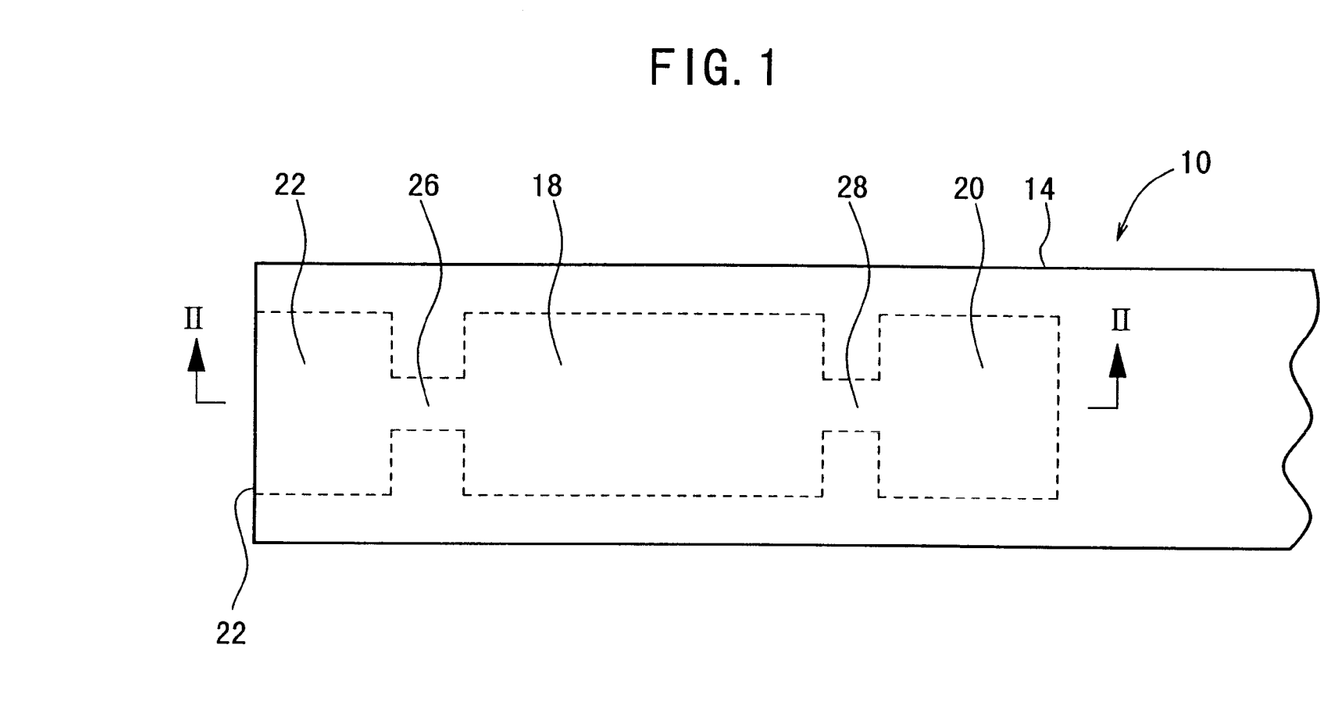
FIG. 1 shows a plan view illustrating an arrangement of a NOx concentration-measuring apparatus according to an embodiment of the present invention.
Figure 2:
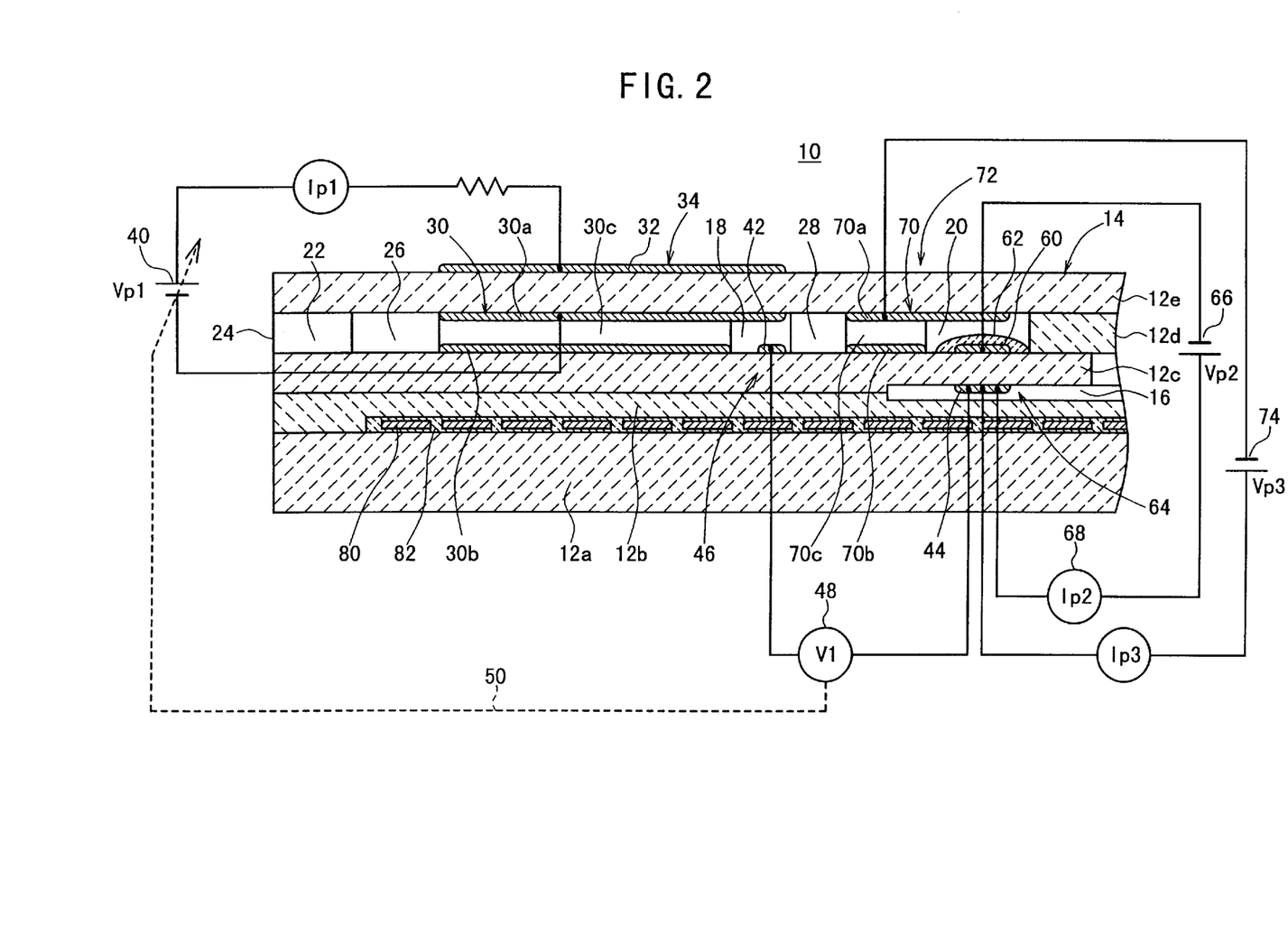
FIG. 2 shows a sectional view taken along a line II—II shown in FIG. 1.

As shown in FIGS. 1 and 2, the NOx concentration-measuring apparatus 10 according to this embodiment has a substrate 14 comprising, for example, five stacked solid electrolyte layers 12a to 12e composed of ceramics based on the use of oxygen ion-conductive solid electrolytes such as $ZrO_2$.

The substrate 14 is constructed as follows. That is, first and second layers from the bottom are designated as first and second substrate layers 12a, 12b respectively. Third and fifth layers from the bottom are designated as first and second solid electrolyte layers 12c, 12e respectively. A fourth layer from the bottom is designated as a spacer layers 12d.

A space (reference gas-introducing space) 16, into which a reference gas such as atmospheric air to be used as a reference for measuring oxides is introduced, is formed between the second substrate layer 12b and the first solid electrolyte layer 12c, the space 16 being comparted by a recess formed on a lower surface of the first solid electrolyte layer 12c and a recess formed on an upper surface of the second substrate layer 12b.

A first chamber 18 for adjusting the partial pressure of oxygen in a measurement gas, and a second chamber 20 for finely adjusting the partial pressure of oxygen in the measurement gas and measuring oxides, for example, nitrogen oxides (NOx) in the measurement gas are formed and comparted between a lower surface of the second solid electrolyte layer 12e and an upper surface of the first solid electrolyte layer 12c.

The NOx concentration-measuring apparatus 10 according to this embodiment has a space section 22 which is formed at a forward end of the spacer layer 12d. A forward end opening of the space section 22 constitutes a gas-introducing port 24. The space section 22 communicates with the first chamber 18 via a first diffusion rate-determining section 26. The first chamber 18 communicates with the second chamber 20 via a second diffusion rate-determining section 28.

In this embodiment, each of the first and second diffusion rate-determining sections 26, 28 gives a predetermined diffusion resistance to the measurement gas to be introduced into the first chamber 18 and the second chamber 20 respectively. In the illustrative arrangement shown in FIG. 1, each of the first and second diffusion rate-determining sections 26, 28 is formed as a vertically extending slit having a predetermined cross-sectional area capable of introducing the measurement gas. Both of the vertically extending slits are formed at substantially central portions of the spacer layer 12d in the widthwise direction.

It is also preferable that a porous member composed of $ZrO_2$ or the like is arranged and packed in the slit of the second diffusion rate-determining section 28 so that the diffusion resistance of the second diffusion rate-determining section 28 is larger than the diffusion resistance of the first diffusion rate-determining section 26. It is preferable that the diffusion resistance of the second diffusion rate-determining section 28 is larger than that of the first diffusion rate-determining section 26. However, no problem occurs even when the former is smaller than the latter.

The atmosphere in the first chamber 18 is introduced into the second chamber 20 under the predetermined diffusion resistance via the second diffusion rate-determining section 28.

The space section 22 functions as a clogging-preventive section for avoiding the clogging of particles (for example, soot and oil combustion waste) produced in the measurement gas in the external space, which would be otherwise caused in the vicinity of the inlet of the first chamber 18. Accordingly, it is possible to measure the NOx component more accurately.

The NOx concentration-measuring apparatus 10 according to this embodiment has an inner pumping electrode 30 which is composed of a porous cermet electrode (for example, a cermet electrode of $Pt.ZrO_2$ containing 1 wt. % Au) formed on an inner wall surface of the first chamber 18. An outer pumping electrode 32 is formed on an upper surface portion corresponding to the inner pumping electrode 30, of the upper surface of the second solid electrolyte layer 12e. An electrochemical pumping cell, i.e., a main pumping cell 34 is constructed by the inner pumping electrode 30, the outer pumping electrode 32, the second solid electrolyte layer 12e interposed between the both electrodes 30, 32, the first solid electrolyte layer 12c, and the spacer layer 12d.

The inner pumping electrode 30 is formed mutually continuously to surround the inner wall surface of the first chamber 18. The inner pumping electrode 30 is constructed by continuously forming an electrode section 30a which is arranged on the lower surface of the second solid electrolyte layer 12e as the upper surface of the wall surface of the first chamber 18, an electrode section 30b which is arranged on the upper surface of the first solid electrolyte layer 12c as the lower surface of the inner wall surface, and electrode sections 30c, 30d (electrode section 30d is not shown) which are arranged on the side surfaces of the spacer layer 12d as the side surfaces of the inner wall surface.

The inner pumping electrode 30 may be constructed by using only any one of the electrode section 30a on the upper surface and the electrode section 30b on the lower surface. Alternatively, the inner pumping electrode 30 may be constructed by using three in total of the electrode sections 30a, 30b on the both upper and lower surfaces and any one of the electrode sections 30c, 30d on the side surfaces.

A desired control voltage (pumping voltage) Vp1 is applied between the inner pumping electrode 30 and the outer pumping electrode 32 of the main pumping cell 34 by the aid of an external variable power source 40 to allow a pumping current Ip1 to flow in a positive or negative direction between the outer pumping electrode 32 and the inner pumping electrode 30. Thus, the oxygen in the atmosphere in the first chamber 18 can be pumped out to the external space, or the oxygen in the external space can be pumped into the first chamber 18.

A measuring electrode 42, which is composed of a porous cermet electrode having a substantially rectangular planar configuration, is formed on a portion of the upper surface of the first solid electrolyte layer 12c for forming the first chamber 18, the upper surface portion being disposed in the vicinity of the second diffusion rate-determining section 28 (the lower surface electrode section 30b of the inner pumping electrode 30 is not formed on the portion). A reference electrode 44 is formed on a lower surface portion exposed to the reference gas-introducing space 16, of the lower surface of the first solid electrolyte layer 12c. An electrochemical sensor cell, i.e., a controlling oxygen partial pressure-detecting cell 46 is constructed by the measuring electrode 42, the reference electrode 44, and the first solid electrolyte layer 12c.

The controlling oxygen partial pressure-detecting cell 46 is operated as follows. That is, an electromotive force is generated between the measuring electrode 42 and the reference electrode 44 on the basis of a difference in oxygen concentration between the atmosphere in the first chamber 18 and the reference gas (atmospheric air) in the reference gas-introducing space 16. The partial pressure of oxygen in the atmosphere in the first chamber 18 can be detected by measuring the electromotive force by using a voltmeter 48.

That is, the voltage V1 generated between the reference electrode 44 and the measuring electrode 42 is an electromotive force of the oxygen concentration cell generated on the basis of the difference between the partial pressure of oxygen of the reference gas introduced into the reference gas-introducing space 16 and the partial pressure of oxygen of the measurement gas in the first chamber 18. The voltage V1 has the following relationship known as the Nernst's equation.

$$V1 = RT/4F \ln(P1(O_2)/P0(O_2))$$

R: gas constant;
T: absolute temperature;
F: Faraday constant;
P1($O_2$): partial pressure of oxygen in the first chamber 18;
P0($O_2$): partial pressure of oxygen of the reference gas.

Therefore, the partial pressure of oxygen in the first chamber 18 can be detected by measuring the voltage V1 generated on the basis of the Nernst's equation by using the voltmeter 48.

The detected value of the partial pressure of oxygen is used to control the pumping voltage of the variable power source 40 by the aid of a feedback control system 50. Specifically, the pumping operation effected by the main pumping cell 34 is controlled so that the partial pressure of oxygen in the atmosphere in the first chamber 18 has a predetermined value which is sufficiently low to control the partial pressure of oxygen in the second chamber 20 in the next step.

Each of the inner pumping electrode 30 and the outer pumping electrode 32 is composed of an inert material having a low catalytic activity on NOx such as NO contained in the measurement gas introduced into the first chamber 18. Specifically, the inner pumping electrode 30 and the outer pumping electrode 32 may be composed of a porous cermet electrode. In this embodiment, the electrode is composed of a metal such as Pt and a ceramic material such as $ZrO_2$. Especially, it is necessary to use a material which has a weak reducing ability or no reducing ability with respect to the NO component in the measurement gas, for the inner pumping electrode 30 and the measuring electrode 42 disposed in the first chamber 18 to make contact with the measurement gas. It is preferable that the inner pumping electrode 30 and the measuring electrode 42 are composed of, for example, a compound having the perovskite structure such as $La_3CuO_4$, a cermet comprising a ceramic material and a metal such as Au having a low catalytic activity, or a cermet comprising a ceramic material, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

The NOx concentration-measuring apparatus 10 according to this embodiment further comprises a detecting electrode 60 having a substantially rectangular planar configuration and composed of a porous cermet electrode, the detecting electrode 60 being formed at an upper surface portion for forming the second chamber 20, separated from the second diffusion rate-determining section 28, of the upper surface of the first solid electrolyte layer 12c. An alumina film, which constitutes a third diffusion rate-determining section 62, is formed to cover the detecting electrode 60. An electrochemical pumping cell, i.e., a measuring pumping cell 64 is constructed by the detecting electrode 60, the reference electrode 44, and the first solid electrolyte layer 12c.

The detecting electrode 60 is composed of a porous cermet comprising zirconia as a ceramic material and a metal capable of reducing NOx as the measurement gas component. Accordingly, the detecting electrode 60 functions as a NOx-reducing catalyst for reducing NOx existing in the atmosphere in the second chamber 20. Further, the oxygen in the atmosphere in the second chamber 20 can be pumped out to the reference gas-introducing space 16 by applying a constant voltage Vp2 between the detecting electrode 60 and the reference electrode 44 by the aid of a DC power source 66. The pumping current Ip2, which is allowed to flow in accordance with the pumping operation performed by the measuring pumping cell 64, is detected by an ammeter 68. Details of the detecting electrode 60 will be described later on.

The constant voltage (DC) power source 66 can apply a voltage of a magnitude to give a limiting current to the pumping for oxygen produced during decomposition in the measuring pumping cell 64 under the inflow of NOx restricted by the third diffusion rate-determining section 62.

On the other hand, an auxiliary pumping electrode 70, which is composed of a porous cermet electrode (for example, a cermet electrode of Pt.$ZrO_2$ containing 1 wt. % Au), is formed on an inner wall surface portion for forming the second chamber 20, of the lower surface of the second solid electrolyte layer 12e. An auxiliary electrochemical pumping cell, i.e., an auxiliary pumping cell 72 is constructed by the auxiliary pumping electrode 70, the second solid electrolyte layer 12e, the spacer layer 12d, the first solid electrolyte layer 12c, and the reference electrode 44.

The auxiliary pumping electrode 70 is based on the use of a material having a weak reducing ability or no reducing ability with respect to the NO component contained in the measurement gas, in the same manner as in the inner pumping electrode 30 of the main pumping cell 34. In this embodiment, for example, it is preferable that the auxiliary pumping electrode 70 is composed of a compound having the perovskite structure such as $La_3CuO_4$, a cermet comprising a ceramic material and a metal having a low catalytic activity such as Au, or a cermet comprising a ceramic material, a metal of the Pt group, and a metal having a low catalytic activity such as Au. Further, when an alloy comprising Au and a metal of the Pt group is used as an electrode material, it is preferable to add Au in an amount of 0.03 to 35% by volume of the entire metal components.

The auxiliary pumping electrode 70 is formed mutually continuously to surround the inner wall surface of the second chamber 20, in the same manner as the inner pumping electrode 30 described above. The auxiliary pumping electrode 70 is constructed by continuously forming an electrode section 70a which is arranged on the lower surface of the second solid electrolyte layer 12e as the upper surface of the wall surface of the second chamber 20, an electrode section 70b which is arranged on the upper surface of the first solid electrolyte layer 12c as the lower surface of the wall surface, and electrode sections 70c, 70d (electrode section 70d is not shown) which are arranged on the side surfaces of the spacer layer 12d as the side surfaces of the wall surface.

The auxiliary pumping electrode 70 may be constructed by using only any one of the electrode section 70a on the upper surface and the electrode section 70b on the lower surface. Alternatively, the auxiliary pumping electrode 70 may be constructed by using three in total of the electrode sections 70a, 70b on the both upper and lower surfaces and any one of the electrode sections 70c, 70d on the side surfaces.

A desired constant voltage Vp3 is applied between the reference electrode 44 and the auxiliary pumping electrode 70 of the auxiliary pumping cell 72 by the aid of an external DC power source 74. Thus, the oxygen in the atmosphere in the second chamber 20 can be pumped out to the reference gas-introducing space 16.

Accordingly, the partial pressure of oxygen in the atmosphere in the second chamber 20 is allowed to have a low value of partial pressure of oxygen at which the measurement of the amount of the objective component is not substantially affected, under the condition in which the measurement gas component (NOx) is not substantially reduced or decomposed. In this embodiment, owing to the operation of the main pumping cell 34 for the first chamber 18, the change in amount of oxygen introduced into the second chamber 20 is greatly reduced as compared with the change in the measurement gas. Accordingly, the partial pressure of oxygen in the second chamber 20 is accurately controlled to be constant.

Therefore, in the case of the NOx concentration-measuring apparatus 10 constructed as described above, the measurement gas, which has been controlled for the partial pressure of oxygen in the second chamber 20, is introduced into the detecting electrode 60.

As shown in FIG. 2, the NOx concentration-measuring apparatus 10 according to this embodiment further comprises a heater 80 for generating heat in accordance with electric power supply from the outside. The heater 80 is embedded in a lower portion of the second substrate layer 12b. The heater 80 is provided in order to increase the conductivity of oxygen ion. A insulative layer 82 composed of alumina or the like is formed to cover upper and lower surfaces of the heater 80 so that the heater 80 is electrically insulated from the first and second substrate layers 12a, 12b.

The heater 80 is arranged over the entire portion ranging from the first chamber 18 to the second chamber 20. Accordingly, each of the first chamber 18 and the second chamber 20 is heated to a predetermined temperature. Simultaneously, each of the main pumping cell 34, the controlling oxygen partial pressure-detecting cell 46, and the measuring pumping cell 64 is also heated to a predetermined temperature and maintained at that temperature.

Next, the operation of the NOx concentration-measuring apparatus 10 according to the embodiment of the present invention will be explained. At first, the forward end of the NOx concentration-measuring apparatus 10 is disposed in the external space. Accordingly, the measurement gas is introduced into the first chamber 18 under the predetermined diffusion resistance via the first diffusion rate-determining section 26. The measurement gas, which has been introduced into the first chamber 18, is subjected to the pumping action for oxygen, caused by applying the predetermined pumping voltage Vp1 between the outer pumping electrode 32 and the inner pumping electrode 30 which construct the main pumping cell 34. The partial pressure of oxygen is controlled to have a predetermined value, for example, $10^{-7}$ atm. The control is performed by the aid of the feedback control system 50.

The first diffusion rate-determining section 26 serves to limit the amount of diffusion and inflow of oxygen in the measurement gas into the measuring space (first chamber 18) when the pumping voltage Vp1 is applied to the main pumping cell 34 so that the current flowing through the main pumping cell 34 is suppressed.

In the first chamber 18, a state of partial pressure of oxygen is established, in which NOx in the atmosphere is not reduced by the inner pumping electrode 30 even in an environment of being heated by the external measurement gas and being heated by the heater 80. For example, a condition of partial pressure of oxygen is formed, in which the reaction of NO→½$N_2$ +½$O_2$ substantially does not occur, because of the following reason. That is, if NOx in the measurement gas (atmosphere) is reduced in the first chamber 18, it is impossible to accurately measure NOx in the second chamber 20 disposed at the downstream stage. In this context, it is necessary to establish a condition in the first chamber 18 in which NOx is not reduced by the component which participates in reduction of NOx (in this case, the metal component of the inner pumping electrode 30). Specifically, as described above, such a condition is achieved by using, for the inner pumping electrode 30, the material having a low ability to reduce NOx, for example, an alloy of Au and Pt.

The gas in the first chamber 18 is introduced into the second chamber 20 under the predetermined diffusion resistance via the second diffusion rate-determining section 28. The gas, which has been introduced into the second chamber 20, is subjected to the pumping action for oxygen, caused by applying the constant voltage Vp3 between the reference electrode 44 and the auxiliary pumping electrode 70 which constitute the auxiliary pumping cell 72 to make fine adjustment so that the partial pressure of oxygen has a constant and low value of partial pressure of oxygen.

The second diffusion rate-determining section 28 serves to limit the amount of diffusion and inflow of oxygen in the measurement gas into the measuring space (second chamber 20) when the constant voltage Vp3 is applied to the auxiliary pumping cell 72 so that the pumping current Ip3 flowing through the auxiliary pumping cell 72 is suppressed, in the same manner as performed by the first diffusion rate-determining section 26.

The measurement gas, which has been controlled for the partial pressure of oxygen in the second chamber 20 as described above, is introduced into the detecting electrode 60 under the predetermined diffusion resistance via the third diffusion rate-determining section 62.

When it is intended to control the partial pressure of oxygen in the atmosphere in the first chamber 18 to have a low value of the partial pressure of oxygen which does not substantially affect the measurement of NOx, by operating the main pumping cell 34, in other words, when the pumping voltage Vp1 of the variable power source 40 is adjusted by the aid of the feedback control system 50 so that the voltage V1 detected by the controlling oxygen partial pressure-detecting cell 46 is constant, if the oxygen concentration in the measurement gas greatly changes, for example, in a range of 0 to 20%, then the respective partial pressures of oxygen in the atmosphere in the second chamber 20 and in the atmosphere in the vicinity of the detecting electrode 60 slightly change in ordinary cases. This phenomenon is caused probably because of the following reason. That is, when the oxygen concentration in the measurement gas increases, the distribution of the oxygen concentration occurs in the widthwise direction and in the thickness direction in the first chamber 18. The distribution of the oxygen concentration changes depending on the oxygen concentration in the measurement gas.

However, in the case of the NOx concentration-measuring apparatus 10 according to this embodiment, the auxiliary pumping cell 72 is provided for the second chamber 20 so that the partial pressure of oxygen in its internal atmosphere always has a constant low value of the partial pressure of oxygen. Accordingly, even when the partial pressure of oxygen in the atmosphere introduced from the first chamber 18 into the second chamber 20 changes depending on the oxygen concentration in the measurement gas, the partial pressure of oxygen in the atmosphere in the second chamber 20 can be always made to have a constant low value, owing to the pumping action performed by the auxiliary pumping cell 72. As a result, the partial pressure of oxygen can be controlled to have a low value at which the measurement of NOx is not substantially affected.

NOx in the measurement gas introduced into the detecting electrode 60 is reduced or decomposed around the detecting electrode 60. Thus, for example, a reaction of NO→½N$_2$ +½O$_2$ is allowed to occur. In this process, a predetermined voltage Vp2, for example, 430 mV (700° C.) is applied between the detecting electrode 60 and the reference electrode 44 which construct the measuring pumping cell 64, in a direction to pump out the oxygen from the second chamber 20 to the reference gas-introducing space 16.

Therefore, the pumping current Ip2 flowing through the measuring pumping cell 64 has a value which is proportional to a sum of the oxygen concentration in the atmosphere introduced into the second chamber 20, i.e., the oxygen concentration in the second chamber 20 and the oxygen concentration produced by reduction or decomposition of NOx by the aid of the detecting electrode 60.

In this embodiment, the oxygen concentration in the atmosphere in the second chamber 20 is controlled to be constant by means of the auxiliary pumping cell 72. Accordingly, the pumping current Ip2 flowing through the measuring pumping cell 64 is proportional to the NOx concentration. The NOx concentration corresponds to the amount of diffusion of NOx limited by the third diffusion rate-determining section 62. Therefore, even when the oxygen concentration in the measurement gas greatly changes, it is possible to accurately measure the NOx concentration, based on the use of the measuring pumping cell 64 by the aid of the ammeter 68.

According to the fact described above, almost all of the pumping current value Ip2 obtained by operating the measuring pumping cell 64 represents the amount brought about by the reduction or decomposition of NOx. Accordingly, the obtained result does not depend on the oxygen concentration in the measurement gas.

The detecting electrode 60 formed in the second chamber will now be explained in detail below. For example, when a cermet electrode of Rh/ZrO$_2$ was used as the detecting electrode 60, a phenomenon was observed, in which the sensitivity was decreased in accordance with the increase in operation time.

This phenomenon was caused by the increase in impedance of the measuring pumping cell 64. When the NOx concentration-measuring apparatus with the increased impedance was observed, it was recognized that the contact area was decreased between the detecting electrode 60 and the first solid electrolyte layer 12c. That is, it is assumed that the increase in impedance is caused by the decrease in contact area between the detecting electrode 60 and the first solid electrolyte layer 12c.

Accordingly, an experiment (conveniently referred to as "first illustrative experiment") was carried out. In the first illustrative experiment, the way of change of the weight of the alloy (sample) composed of Pt and Rh depending on the increase in heat was measured by using a thermo-balance while changing the weight ratio between Pt and Rh. Obtained results are shown in FIG. 3.

Figure 3:
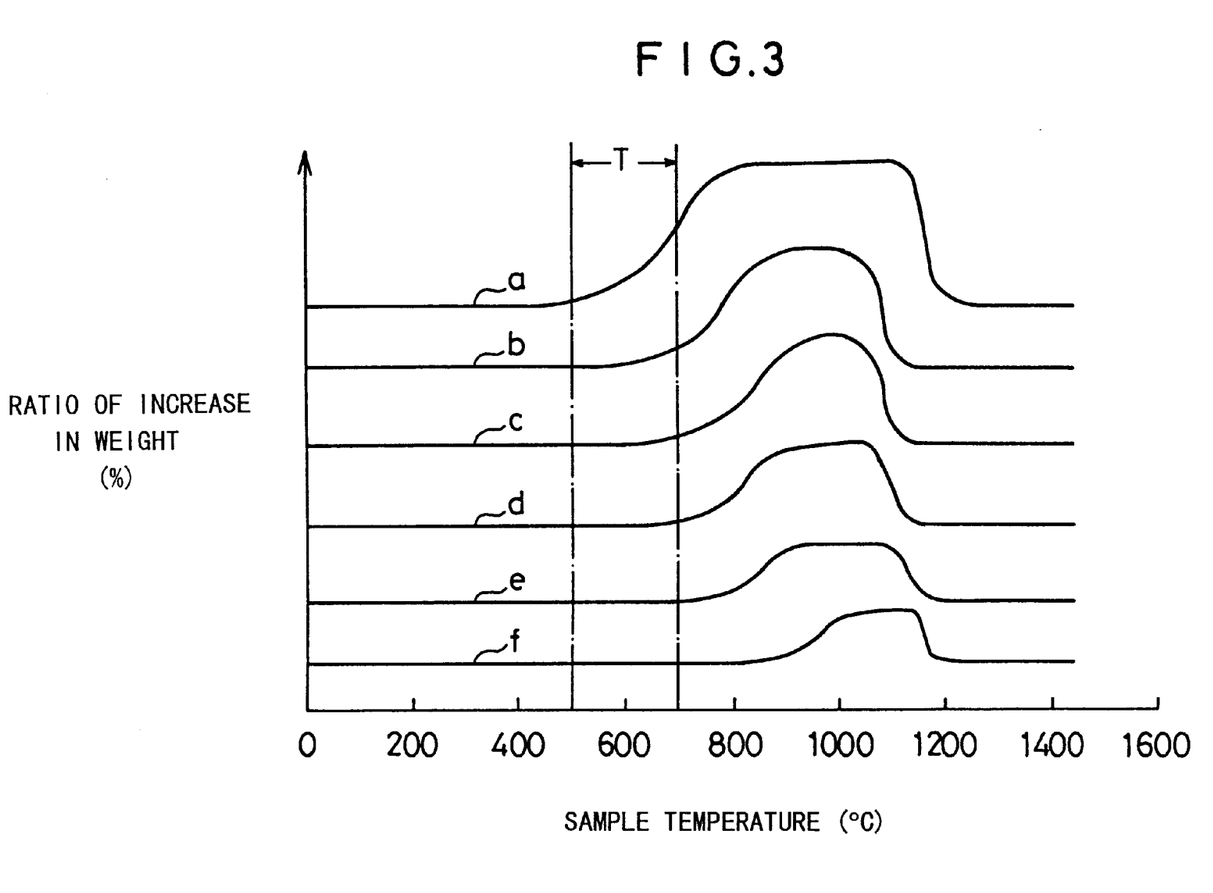
FIG. 3 shows characteristic curves illustrating results obtained in a first illustrative experiment (illustrative experiment to measure the way of change of the weight of the alloy composed of Rh and Pt depending on the increase in heat, by changing the weight ratio between Rh and Pt)

In FIG. 3, a curve "a" represents a characteristic in the case of Rh=100 wt. %. A curve "b" represents a characteristic in the case of Pt/Rh=1 wt. %/99 wt. %. A curve "c" represents a characteristic in the case of Pt/Rh=5 wt. %/95 wt. %. A curve "d" represents a characteristic in the case of Pt/Rh=10 wt. %/90 wt. %. A curve "e" represents a characteristic in the case of Pt/Rh=20 wt. %/80 wt. %. A curve "f" represents a characteristic in the case of Pt/Rh=25 wt. %/75 wt. %.

According to the experimental result shown in FIG. 3, it is understood that in the case of Rh=100 wt. % (curve "a"), the weight increase caused by the oxidation of Rh (Rh$_2$O$_3$) is observed in a range from about 500° C. to about 800° C., the weight is decreased as the metallization is started again from about 1100° C., and the weight is returned to the original weight at about 1200° C.

Similarly, it is understood that in the case of Pt/Rh=1 wt. %/99 wt. % (curve "b"), the weight increase caused by the oxidation of Rh ($Rh_2O_3$) is observed in a range from about 600° C. to about 900° C., the weight is decreased as the metallization is started again from about 1000° C., and the weight is returned to the original weight at about 1150° C.

Figure 4:
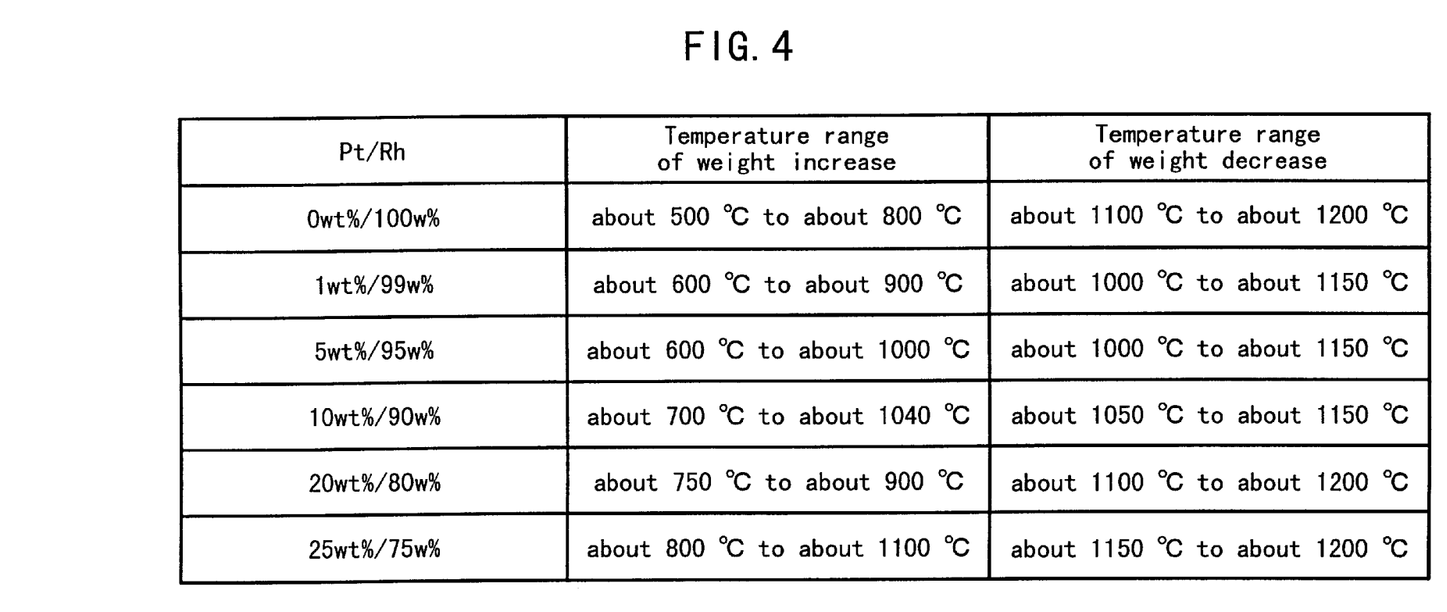
FIG. 4 shows a table illustrating the range of increase in weight brought about by the oxidation of alloy composed of Rh and Pt, and the range of decrease in weight brought about by the reconversion into the metal, in the first illustrative experiment.

FIG. 4 summarizes the range of weight increase caused by the oxidation, and the range of the weight decrease caused by the reconversion into metal as described above.

According to FIGS. 3 and 4, it is understood that in the case of the detecting electrode of Rh=100 wt. % (curve "a"), the weight increase, i.e., the volume increase remarkably occurs in the operation temperature range of 500° C. to 700° C.

The practical use or operation of the NOx concentration-measuring apparatus 10 is usually carried out by setting the element temperature at about 700° C. Therefore, for example, if the detecting electrode 60 is constructed by using the cermet electrode of Rh=100 wt. % (curve "a"), the volume decrease occurs due to the reconversion into metal of Rh as caused by the oxygen pumping effected by the detecting electrode 60 during the operation of the sensor. The oxidation of Rh ($Rh_2O_3$) occurs immediately after the stop of the operation of the sensor, because the element temperature is still not less than 600° C. although the oxygen pumping is stopped, resulting in the occurrence of the volume increase of Rh.

When the series of volume increase and volume decrease are repeated, then the detecting electrode 60 is partially peeled off from the first solid electrolyte layer 12c, and the contact area is decreased between the detecting electrode 60 and the first solid electrolyte layer 12c. In this situation, it is postulated that the impedance of the measuring pumping cell 64 is increased, and the sensitivity to NOx is decreased.

However, as understood from FIG. 3, when the detecting electrode 60 is constructed by using the cermet electrode which is composed of the alloy of Pt—Rh and the ceramic component, the volume increase occurs in the range deviated from the operation temperature range T. Therefore, the peeling off phenomenon as described above is not caused by the detecting electrode 60. That is, it is possible to suppress the oxidation reaction and the reduction reaction of Rh in the practical use.

Figure 5:
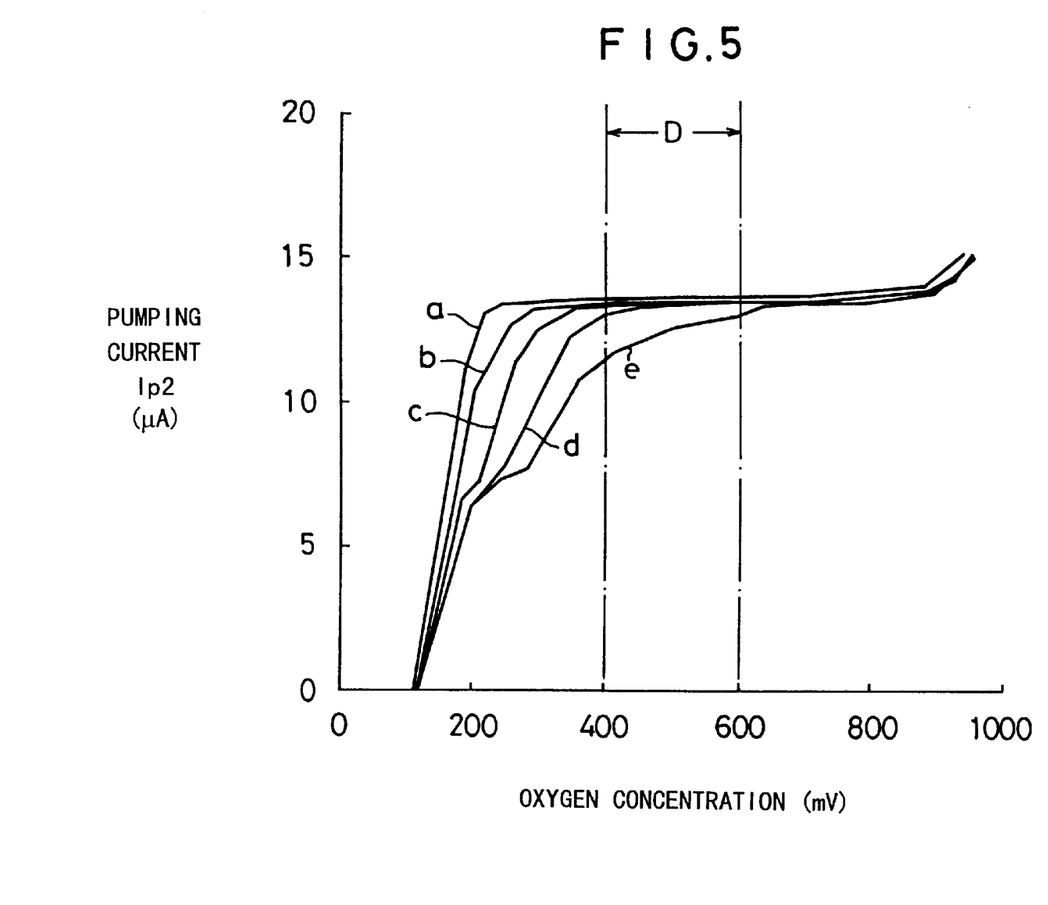
FIG. 5 shows limiting current characteristics obtained when the heat is applied in the atmospheric air at 700° C. in a second illustrative experiment.

Another illustrative experiment (conveniently referred to as "second illustrative experiment") was carried out, in which NOx concentration-measuring apparatuses 10 were manufactured while changing the ratio of Pt/Rh contained in the detecting electrode 60 respectively. Limiting current characteristics, which were obtained when the NO concentration was 1000 ppm, were plotted for the five NOx concentration-measuring apparatuses 10. FIG. 5 shows the limiting current characteristics which were obtained when the heat was applied to an element (substrate 14) to be a temperature of 700° C.

In FIG. 5, a curve "a" represents a characteristic in the case of Rh=100 wt. %. A curve "b" represents a characteristic in the case of Pt/Rh=1 wt. %/99 wt. %. A curve "c" represents a characteristic in the case of Pt/Rh=10 wt. %/90 wt. %. A curve "d" represents a characteristic in the case of Pt/Rh=20 wt. %/80 wt. %. A curve "e" represents a characteristic in the case of Pt/Rh=25 wt. %/75 wt. %.

The horizontal axis represents the electromotive force of the oxygen concentration cell, generated on the basis of the difference between the partial pressure of oxygen of the reference gas to be introduced into the reference gas-introducing space 16 and the partial pressure of oxygen in the atmosphere to make contact with the detecting electrode 60 disposed in the second chamber 20. The horizontal axis equivalently corresponds to the oxygen concentration of the measurement gas.

According to FIG. 5, in the second illustrative experiment, an approximately constant pumping current (pumping current corresponding to a NO concentration =1000 ppm) flows in each of the apparatuses corresponding to Rh=100% (curve "a"), Pt/Rh=1 wt. %/99 wt. % (curve "b"), Pt/Rh=10 wt. %/90 wt. % (curve "c"), and Pt/Rh=20 wt. %/80 wt. % (curve "d"), in a substantial detection range D (400 mV to 600 mV). Therefore, it is understood that NOx can be accurately measured in the case of these apparatuses.

Although the apparatus, which corresponds to Pt/Rh=25 wt. %/75 wt. % (curve "e"), involves no problem in view of the practical use, it is feared that the pumping current somewhat disperses in this apparatus, and it is difficult for this apparatus to obtain a certain accuracy for the measurement of NOx.

Such a fear may be caused because the cermet electrode of this apparatus, which is composed of the alloy of Pt—Rh and the ceramic component, is inferior in NOx-decomposing/reducing ability as compared with the Rh cermet electrode.

Thus, in this embodiment, it is approved that the detecting electrode 60 is constructed by using the cermet electrode composed of the alloy of Pt—Rh and the ceramic component, and the optimum value of the amount of addition of Rh in the Pt—Rh alloy is such that the ratio of Pt and Rh is Pt:Rh=20:80 to 1:99, preferably Pt:Rh=10:90 to 1:99 in weight ratio.

An illustrative experiment (conveniently referred to as "third illustrative experiment") will now be described. In the third illustrative experiment, NOx concentration-measuring apparatuses 10 were manufactured while changing the ratio of Pt/Rh contained in the detecting electrode 60 respectively. Observation was made for the change in sensitivity to NOx during the practical use of the five NOx concentration-measuring apparatuses 10. Experimental results are shown in FIG. 6.

Figure 6:
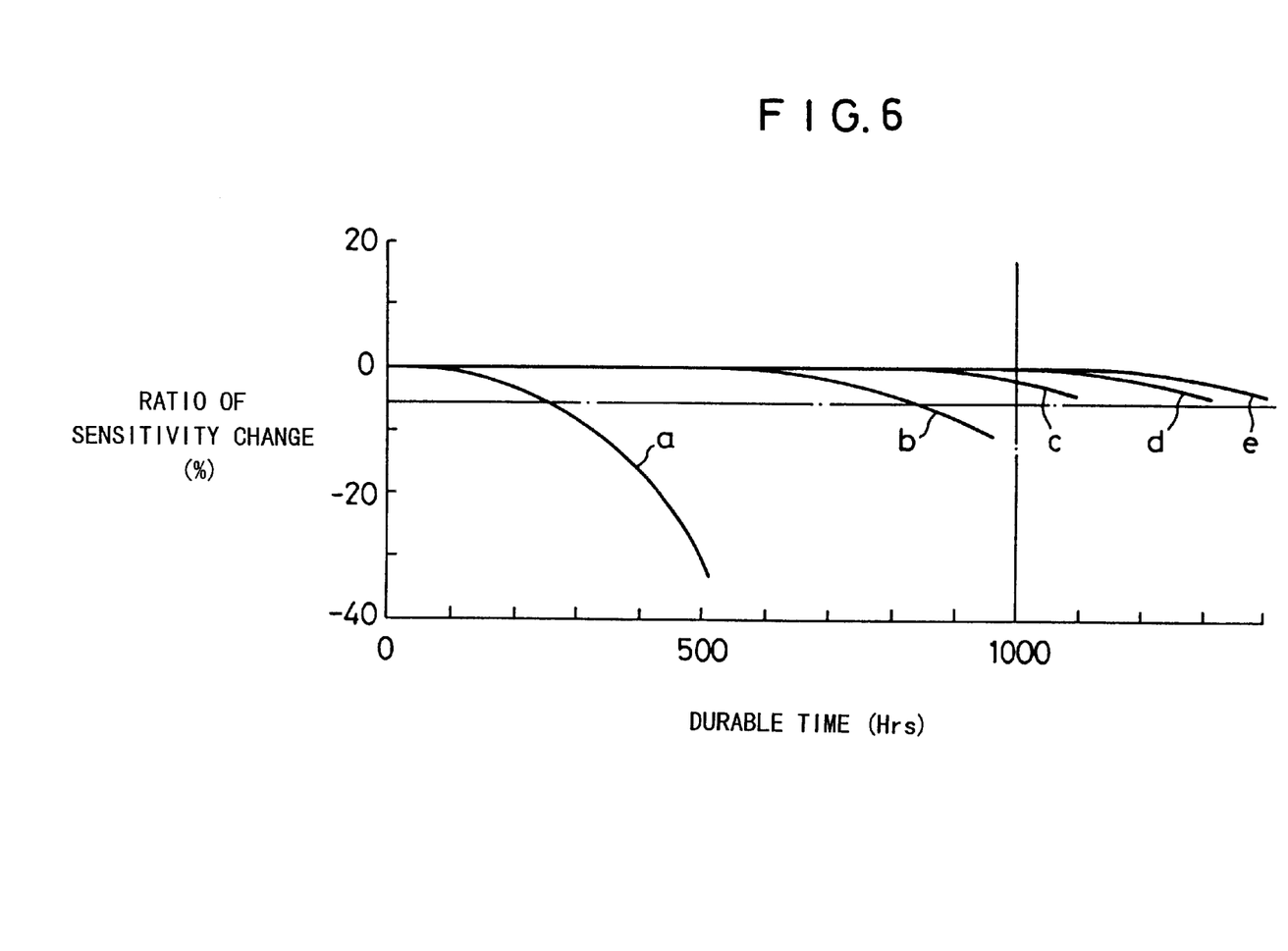
FIG. 6 shows characteristic curves illustrating results obtained in a third illustrative experiment (illustrative experiment to observe the change of sensitivity to NOx with respect to the durable time)

In FIG. 6, a curve "a" represents a characteristic in the case of Rh=100 wt. %. A curve "b" represents a characteristic in the case of Pt/Rh=25 wt. %/75 wt. %. A curve "c" represents a characteristic in the case of Pt/Rh=20 wt. %/80 wt. %. A curve "d" represents a characteristic in the case of Pt/Rh=10 wt. %/90 wt. %. A curve "e" represents a characteristic in the case of Pt/Rh=1 wt. %/99 wt. %.

The following judgement may be acknowledged in the third illustrative experiment. That is, those in which the ratio of sensitivity change is not deteriorated up to −6% at a point of time at which the durable time exceeds 1000 hours are durable. Those in which the ratio of sensitivity change exceeds −6% at a point of time at which the durable time exceeds 1000 hours are not durable.

Based on this judgement standard, it is understood that the apparatus corresponding to Rh=100 wt. % (curve "a") is fairly inferior in durability, because the ratio of sensitivity change is deteriorated up to −6% after the passage of about 250 hours from the start of the experiment. It is understood that the apparatus corresponding to Pt/Rh=25 wt. %/75 wt. % (curve "b") is slightly inferior in durability, because the ratio of sensitivity change is deteriorated up to −6% after the passage of about 820 hours from the start of the experiment.

On the other hand, it is understood that the apparatuses corresponding to Pt/Rh=20 wt. %/80 wt. % (curve "c"), Pt/Rh=10 wt. %/90 wt. % (curve "d"), and Pt/Rh=1 wt. %/99 wt. % (curve "e") are excellent in durability, because the ratio of sensitivity change is not deteriorated up to −6% even after the passage of 1000 hours from the start of the experiment.

As described above, the NOx concentration-measuring apparatus 10 according to the embodiment of the present invention uses the cermet electrode composed of the alloy of Pt—Rh and the ceramic component, as the detecting electrode 60 for constructing the measuring pumping cell 64. Therefore, the oxidation and the reconversion into metal of Rh contained in the detecting electrode 60 are suppressed. Even when the operation time of the NOx concentration-measuring apparatus 10 is increased, the increase in impedance is not brought about, which would be otherwise caused by the decrease in contact area between the detecting electrode 60 and the first solid electrolyte layer 12c.

In this embodiment, the ratio between Pt and Rh is Pt:Rh=20:80 to 1:99, preferably Pt:Rh=10:90 to 1:99 in weight ratio. Therefore, it is possible to suppress the adsorption of NOx at a low temperature and the formation of alloy together with any other metal element (for example, Au), and it is possible to remarkably improve the durability.

In other words, the NOx concentration-measuring apparatus 10 according to this embodiment makes it possible to stabilize the impedance and stabilize the measurement sensitivity.

Next, a modified embodiment of the NOx concentration-measuring apparatus 10 according to the embodiment of the present invention will be explained with reference to FIG. 7. Components or parts corresponding to those shown in FIG. 1 are designated by the same reference numerals.

Figure 7:
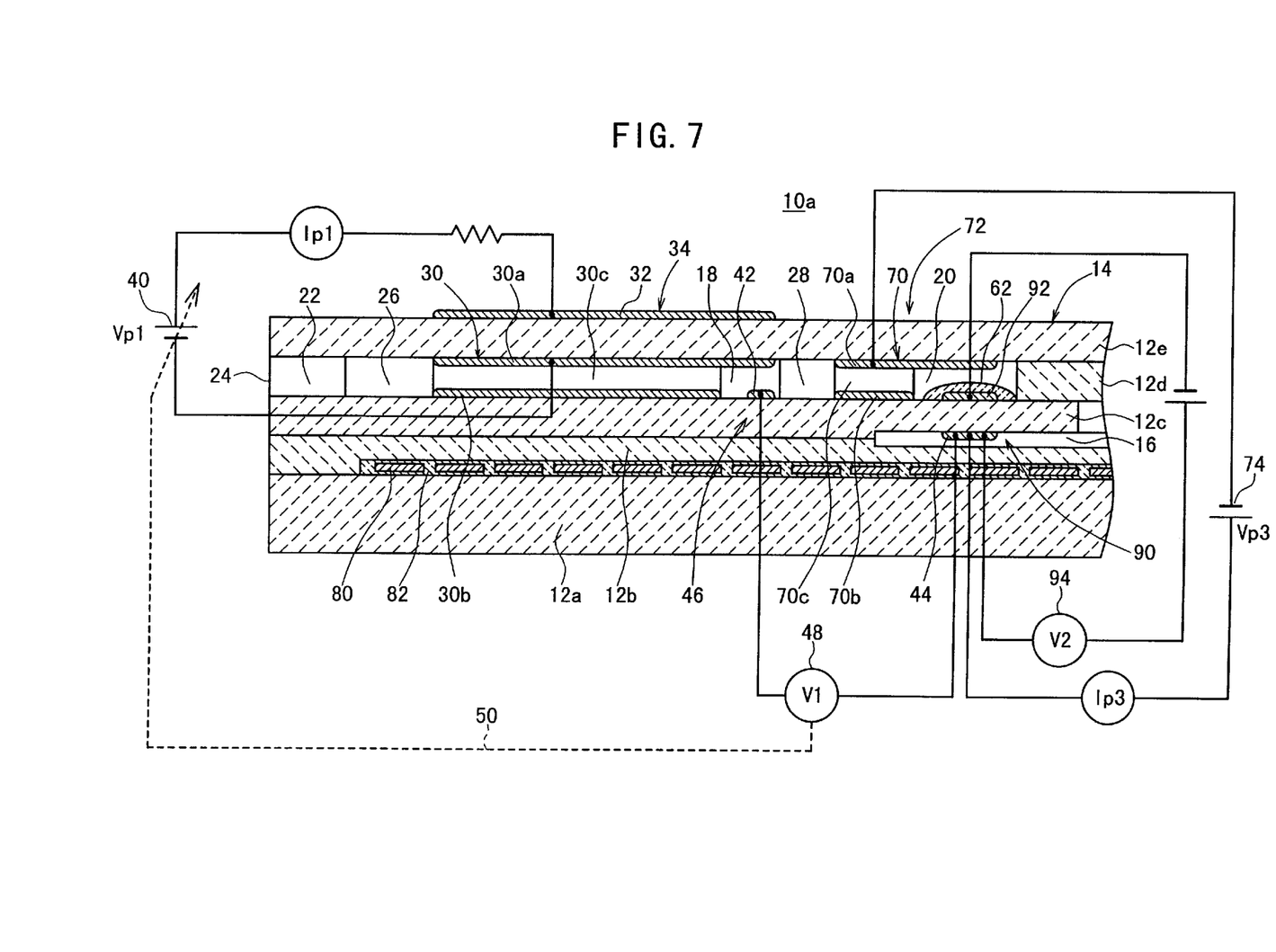
FIG. 7 shows a sectional view illustrating a modified embodiment of the NOx concentration-measuring apparatus according to the embodiment of the present invention.

As shown in FIG. 7, the NOx concentration-measuring apparatus 10a according to this modified embodiment is constructed in approximately the same manner as in the NOx concentration-measuring apparatus 10 according to the foregoing embodiment (see FIG. 2). However, the former is different from the latter in that a measuring oxygen partial pressure-detecting cell 90 is provided in place of the measuring pumping cell 64.

The measuring oxygen partial pressure-detecting cell 90 comprises a detecting electrode 92 formed on an upper surface portion for forming the second chamber 20, of the upper surface of the first solid electrolyte layer 12c, the reference electrode 44 formed on the lower surface of the first solid electrolyte layer 12c, and the first solid electrolyte layer 12c interposed between the both electrodes 92, 44.

In this embodiment, an electromotive force (electromotive force of an oxygen concentration cell) V2 corresponding to the difference in oxygen concentration between the atmosphere around the detecting electrode 92 and the atmosphere around the reference electrode 44 is generated between the reference electrode 44 and the detecting electrode 92 of the measuring oxygen partial pressure-detecting cell 90.

Therefore, the partial pressure of oxygen in the atmosphere around the detecting electrode 92, in other words, the partial pressure of oxygen defined by oxygen produced by reduction or decomposition of the measurement gas component (NOx) is detected as a voltage value by measuring the electromotive force (voltage V2) generated between the detecting electrode 92 and the reference electrode 44 by using a voltmeter 94.

The NOx concentration-measuring apparatus 10a according to this modified embodiment also uses the cermet electrode composed of the alloy of Pt—Rh and the ceramic component, as the detecting electrode 92 for constructing the measuring oxygen partial pressure-detecting cell 90. As a result, the oxidation and the reconversion into metal of Rh contained in the detecting electrode 92 are suppressed. Even when the operation time of the NOx concentration-measuring apparatus 10a is increased, the increase in impedance is not brought about, which would be otherwise caused by the decrease in contact area between the detecting electrode 92 and the first solid electrolyte layer 12c.

Also in the NOx concentration-measuring apparatus 10a according to this modified embodiment, the ratio between Pt and Rh is Pt:Rh=20:80 to 1:99, preferably Pt:Rh=10:90 to 1:99 in weight ratio. Therefore, it is possible to suppress the adsorption of NOx at a low temperature and the formation of alloy together with any other metal element (for example, Au), and it is possible to remarkably improve the durability.

It is a matter of course that the NOx-decomposing electrode and the NOx concentration-measuring apparatus according to the present invention are not limited to the embodiments described above, which may be embodied in other various forms without deviating from the gist or essential characteristics of the present invention.

What is claimed is:

1. A NOx concentration measuring apparatus for measuring a NOx concentration of a measurement gas, comprising:

an oxygen pump cell having a first internal space into which a measurement gas is introduced, said oxygen pump cell including at least one pump electrode in communication with said first internal space, said pump electrode exhibiting substantially no or low decomposing/reducing ability with respect to NOx;

an electrochemical cell having a second internal space and at least a NOx decomposing electrode in communication with said second internal space, said NOx-decomposing electrode comprising a cermet electrode composed of a Pt—Rh alloy having a weight ratio of Pt:Rh in a range of from 20:80 to 1:99 and a ceramic component, and further comprising a porous layer over the NOx decomposing electrode;

a fluid communication path within said apparatus for providing fluid communication between said first and second internal spaces;

wherein said oxygen pump cell controls an oxygen concentration in the measurement gas within said first internal space to have a predetermined value at which NO remains, and said NOx decomposing electrode decomposes NOx within said second internal space to measure the NOx concentration of the measurement gas.

2. The NOx concentration measuring apparatus according to claim 1, wherein said weight ratio of Pt:Rh is in a range of from 10:90 to 1:99.

* * * * *